US005540889A

United States Patent [19]
Gordon et al.

[11] Patent Number: 5,540,889
[45] Date of Patent: Jul. 30, 1996

[54] APPARATUS AND METHOD FOR A HIGHLY PARALLEL PIPETTER

[75] Inventors: Steven J. Gordon, Boston; Anthony J. Christopher, Andover, both of Mass.

[73] Assignee: Whitehead Institute for Biomedical Research, Cambridge, Mass.

[21] Appl. No.: 240,848

[22] Filed: May 11, 1994

[51] Int. Cl.$^6$ .................................................. B01L 3/02
[52] U.S. Cl. .................. 422/100; 73/863.32; 73/864.14; 73/864.13
[58] Field of Search .................. 422/100; 73/863.32, 73/864.14, 864.13

[56] References Cited

U.S. PATENT DOCUMENTS

| | | | |
|---|---|---|---|
| 2,857,082 | 10/1958 | Perkins | 222/255 |
| 3,067,786 | 12/1962 | Rosen | 141/179 |
| 3,447,576 | 6/1969 | Grönlund | 141/167 |
| 3,568,735 | 6/1968 | Lancaster | 141/238 |
| 3,650,306 | 3/1972 | Lancaster | 141/238 |
| 3,683,977 | 8/1972 | Crowe et al. | 141/130 |
| 3,855,868 | 12/1994 | Sudvaniemi | 73/425.6 |
| 3,982,438 | 9/1976 | Byrd | 73/425.6 |
| 4,047,438 | 9/1977 | Sekine | 73/423 A |
| 4,106,911 | 8/1978 | Marcelli | 23/259 |
| 4,116,247 | 9/1978 | Zanasi | 141/392 |
| 4,158,035 | 6/1979 | Haase et al. | 422/100 |
| 4,215,092 | 7/1980 | Suovaniemi | 422/100 |
| 4,228,922 | 10/1980 | Takeshita | 222/47 |
| 4,258,761 | 3/1981 | Bennett, Jr. | 141/242 |
| 4,335,621 | 6/1982 | Tervamaki et al. | 73/863.32 |
| 4,444,062 | 4/1984 | Bennett et al. | 73/863.32 |
| 4,459,864 | 7/1984 | Cirincione | 73/863.32 |
| 4,498,510 | 2/1985 | Minshew, Jr. et al. | 141/27 |
| 4,519,258 | 5/1985 | Jakubowicz | 73/864 |
| 4,554,839 | 11/1985 | Hewett et al. | 73/864.16 |
| 4,599,220 | 7/1986 | Yonkers et al. | 422/100 |
| 4,734,261 | 3/1988 | Koizumi et al. | 422/100 |
| 4,779,467 | 10/1988 | Rainin et al. | 73/864.17 |
| 4,801,434 | 1/1989 | Kido | 422/100 |
| 4,824,642 | 4/1989 | Lyman et al. | 422/100 |
| 4,830,832 | 5/1989 | Arpagaus et al. | 422/65 |
| 4,833,384 | 5/1989 | Munro et al. | 318/687 |
| 4,925,629 | 5/1990 | Schramm | 422/82.05 |
| 5,021,217 | 7/1991 | Oshikubo | 422/100 |
| 5,055,263 | 10/1991 | Meltzer | 422/65 |
| 5,057,281 | 10/1991 | Torti et al. | 422/100 |
| 5,061,449 | 10/1991 | Torti et al. | 422/100 |
| 5,092,184 | 3/1992 | Goodell et al. | 73/863.32 |
| 5,306,510 | 4/1994 | Meltzer | 422/65 |

FOREIGN PATENT DOCUMENTS 1601242  10/1981  United Kingdom .

OTHER PUBLICATIONS

Cole–Parmer Micro–and Macropipettors Order Catalogue, pp. 265–257, 266–267 and 274–275.
Coster Catalogue, "Transtar®–96", p. 30.

*Primary Examiner*—Jill Warden
*Assistant Examiner*—Sharidan Carrillo
*Attorney, Agent, or Firm*—Hamilton, Brook, Smith & Reynolds, P.C.

[57] ABSTRACT

An actuator operates an upper plate assembly which holds a plurality of metal rods, such that all the rods are moved together along parallel longitudinal axes into respective tubes. The plurality of tubes is held by a lower plate assembly, a different tube for each rod. Liquid (sample fluid) is drawn into the individual tubes by the actuator raising the upper plate assembly with respect to the lower plate assembly and hence causing the rods to simultaneously traverse the length of the respective tubes from the distal ends of the tubes to the proximal ends of the tubes. The collected liquid is dispensed by the actuator lowering the upper plate assembly such that the metal rods are simultaneously lowered into the corresponding tubes. The rods are lowered very rapidly and stopped abruptly. This imparts sufficient velocity to the collected sample fluid within the tubes such that the samples under inertia separate from and cleanly exit the distal ends of the tubes. As such, low volume (microvolume) dispenses are enabled in a manner free of sample contact with the target (receiving) tray.

10 Claims, 3 Drawing Sheets

APPARATUS AND METHOD FOR A HIGHLY PARALLEL PIPETTER

BACKGROUND

In chemical and biological laboratories, sample transfer from a source plate to a target plate (or piece of lab ware) is a fundamental task. Typically a pipette or pipetter system is used to (i) collect a desired sample from the source piece of lab ware which holds the sample in one array format, and (ii) deliver/dispense the collected sample to the target piece of lab ware in the same or another array format. Current pipetter systems generally use pistons with seals to move a volume of air in and out of the piston cylinder. The air is used as the working fluid to draw the sample in or out of the pipetter (piston cylinder). Models of various systems are available with multiple pistons (up to 12 pistons, such as the Finnpipette from Labsystems, Inc.) which are aligned in a row at standard 9 mm spacing for filling single rows of microtitration plates. The various pipetter systems are available in models which are manually actuated with a thumb pushbutton, or automatically actuated with a motor.

Another piperting device (such as the one designed by Robbins Scientific, Inc.) uses several Hamilton syringes positioned together in a holder. The Hamilton syringes are extremely precise glass syringe systems with an elastomer air tight seal, and a thin hypo-tube tip. An array of these syringes requires large actuation forces because of the friction in the seals, and the array density is limited by the width of the glass syringes. The cost of each such syringe is also high due to the precise machining of the glass.

In addition preexisting piperting systems used for small volume samples (less than about 10 μl) have a disadvantage in dispensing collected samples. In order to dispense a collected sample, the sample must be touched to a portion of a target plate in order to release the sample from the pipette.

Accordingly, improvements are needed in pipetter systems. And in particular, improvement is needed in such pipette systems used for transferring several samples in an array format from one piece of lab ware to another in a potentially different array format.

SUMMARY OF THE INVENTION

The present invention provides a pipetter system which solves the problems of the prior art. In particular, the present invention pipetter system is designed to reduce manual labor and cost in transferring several chemical and biological samples in an array format from one piece of lab ware to another having the same or different array format.

By way of summary, an actuator operates an upper plate assembly which holds a plurality of metal rods, such that all the rods are moved together along parallel longitudinal axes into respective tubes. The plurality of tubes is held by a lower plate assembly, a different tube for each rod. Liquid (sample fluid) is drawn into the individual tubes by the actuator raising the upper plate assembly with respect to the lower plate assembly, and hence causing the rods to simultaneously traverse the length of the respective tubes from the distal ends of the tubes to the proximal ends of the tubes. The collected liquid is dispensed by the actuator lowering the upper plate assembly such that the metal rods are simultaneously lowered into the corresponding tubes. In order to assure that all collected liquid is dispensed (especially for low volume dispenses), the actuator is lowered very rapidly and stopped abruptly. In turn, the upper plate assembly and hence the rods are lowered very rapidly and stopped abruptly. This imparts a high velocity to the collected sample fluid within the tubes. As such, the samples use their own inertia to separate from and cleanly exit the distal ends of the tubes. Said another way, sufficient velocity is imparted to the collected liquid to enable the collected liquid/samples to cleanly exit the tubes.

In a preferred embodiment the actuator operates along a longitudinal axis and the upper plate assembly lies in a plane perpendicular to the longitudinal axis. The lower plate assembly lies in a plane spaced apart from and parallel to the plane of the upper plate assembly. The tubes receive the respective rods through the proximal ends of the tubes, and the rods and respective tubes are axially aligned with each other. Further, the rods (i.e. working distal ends or tips thereof) are in direct contact with collected liquid.

In another aspect of the present invention, a spring mechanism and an adjustable stop are coupled to the actuator. The spring mechanism enables the actuator to move the upper plate assembly away from the lower plate assembly and hence move the rods such that they traverse the length of the respective tubes from the distal ends to the proximal ends of the tubes for collecting sample fluid in each tube. The adjustable stop defines the stopping position of the upper plate assembly, and in turn determines the amount of sample fluid able to be collected in the tubes. In the preferred embodiment, the adjustable stop is user setable, i.e., set and reset by the user before each use of the pipetter system.

As to another aspect of the present invention, the rods have an outer diameter on the order of 1000th of an inch smaller than the inner diameter of the respective tubes. As such, when the rods traverse the length of the respective tubes, each rod has a gap between it and the respective tube. That is, the gap is sufficiently small/tight such that a seal is formed with the fluid. This enables the tubes to be sealless (i.e. free of physical or mechanical seals).

In the preferred embodiment, the lower plate assembly holds the tubes with chamfered holes, one hole for each tube. The chamfered holes enable sample fluid from respective rods to be funneled into the tubes.

According to another aspect of the present invention the actuator is of pneumatic, manual or motorized operation.

Another feature of the present invention provides alignment pins extending from the lower plate assembly and a tray holder. The tray holder has (i) a recessed area for holding a subject tray, the tray having a plurality of predefined work areas, and (ii) a plurality of holes outside and about the recessed area for receiving the alignment pins of the lower plate assembly. As such, the alignment pins of the lower plate assembly are placed in the holes of the tray holder, and as a result, the distal ends of the tubes are aligned with and face the predefined work areas of the tray. When the alignment pins are positioned in certain ones of the holes of the tray holder, the tubes are aligned with a subset of the work areas of the tray for dispensing thereto. Different holes about the recessed area receive the alignment pins to align the tubes with different subsets of the work areas of the subject tray.

In addition, a working block may be placed under the subject tray in the recessed area of the tray holder. This elevates or raises the subject tray such that the work areas are positioned closer to the distal ends of the tubes.

In another aspect of the present invention, a bracket is coupled to the upper plate assembly for removable coupling of the upper plate assembly to the actuator.

Another feature of the present invention provides a housing about the actuator, upper plate assembly and lower plate assembly. The housing provides a handle for enabling easy hand held use of the present invention pipetter system.

BRIEF DESCRIPTION OF THE DRAWINGS

The foregoing and other objects, features and advantages of the invention will be apparent from the following more particular description of preferred embodiments of the drawings in which like reference characters refer to the same parts throughout the different views. The drawings are not necessarily to scale, emphasis instead being placed upon illustrating the principles of the invention.

DETAILED DESCRIPTION OF THE PRESENT INVENTION

As used herein the terms "parallel pipetter" and "parallel pipetting", and the like mean simultaneous operation of a plurality of pipettes or similar devices. Said another way, these terms mean the collective operation of a plurality of pipettes (i.e., operation at the same time as opposed to a serial or one-at-a-time operation).

As used herein the terms "microamount", "microvolume" and similar language means small volumes on the order of a microliter. In particular, volumes in the range of about ½ µl to 10 µl is intended.

Applicants have discovered a parallel pipetter system which does not depend on air as the working fluid in each pipette of the system. Instead Applicants minimize/omit the air gap between the subject sample and piston such that the piston is in direct contact with the sample. In turn, this eliminates the mechanical capacitance of air and ensures high acceleration of the sample such that highly accurate dispensing is achieved as follows. When dispensing collected samples, the piston moves the sample at a high velocity and abruptly stops at the distal (dispensing) end of the piston cylinder. There is no air gap to absorb the change in motion (i.e., deceleration) of the piston, and hence the energy of the once moving piston is imparted to the sample. As a consequence, the inertia of the sample creates a clean break of the sample from the piston (i.e., break in surface tension with the piston) and piston cylinder, and hence an accurate dispensing of the sample.

Figure 1A:
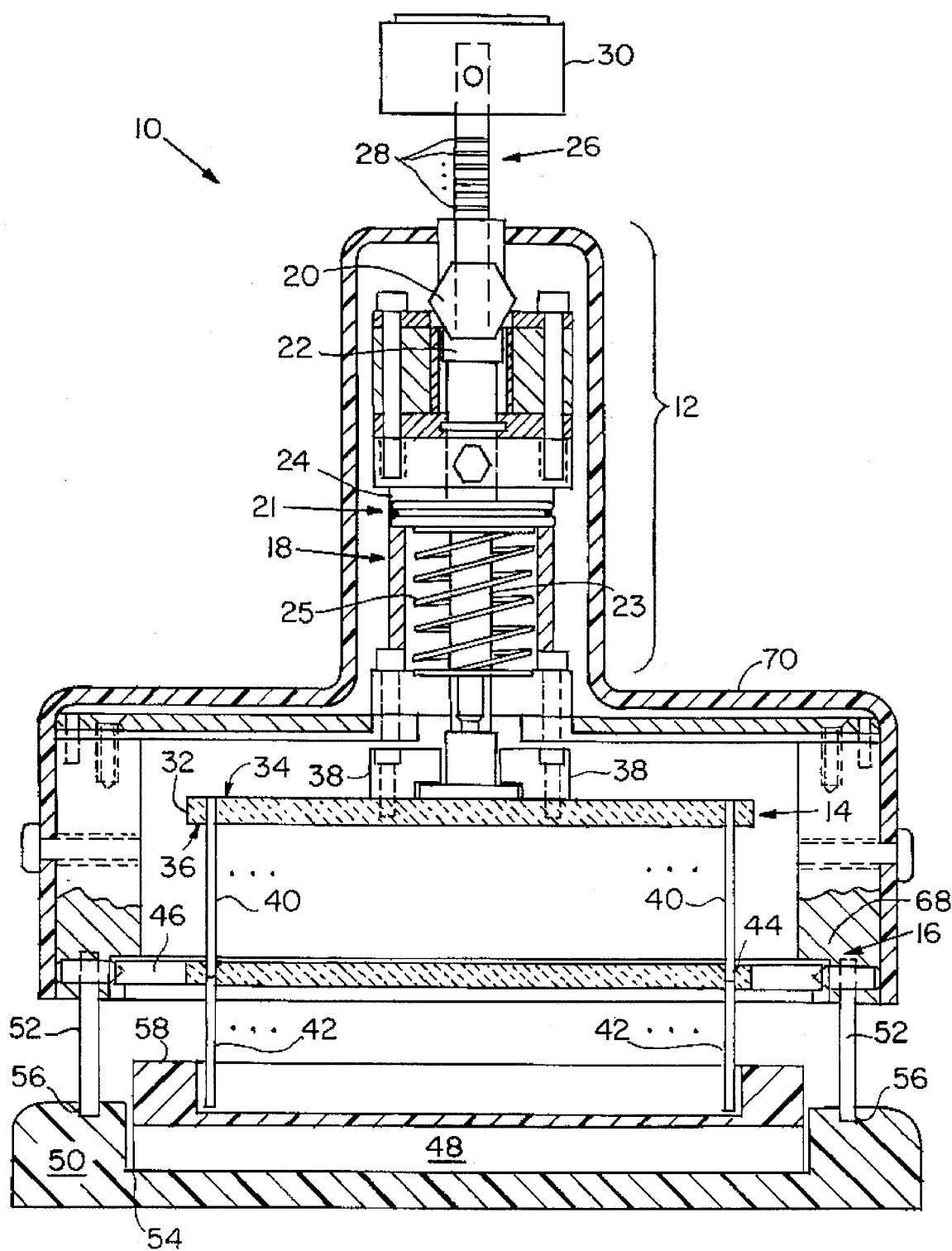
FIGS. 1a–1b are schematic diagrams of one embodiment of the present invention.
Figure 2:
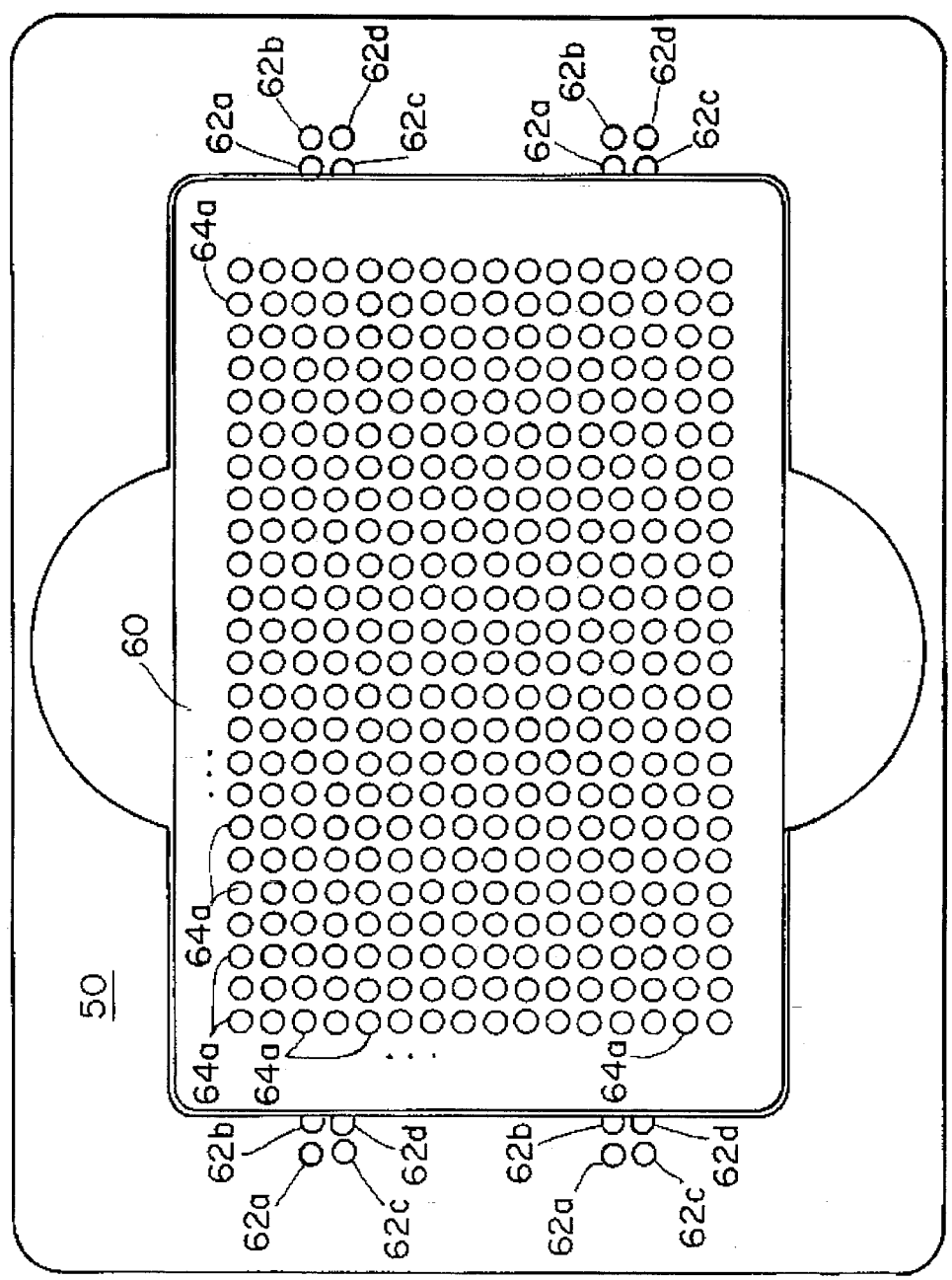
FIG. 2 is a plan view of a plate holder of the embodiment of FIGS. 1a–1b.

The foregoing is realized in the embodiment illustrated in FIGS. 1a–2. That embodiment provides an 8×12 array of pipettes designed to fit standard titration plates having wells (i.e., predefined work areas) arranged in the same format as used by, for example, biological laboratories. It is understood that other pipette arrangements/arrays may be used in other embodiments of the present invention. The below described and illustrated array/arrangement is for illustration purposes and not a limiting factor of the present invention.

The illustrated pipetter system 10 includes a main shaft area 12, an upper plate assembly 14 and a lower plate assembly 16. The main shaft area 12 is formed of an actuator 18 and a repositionable stop 24. As described below in greater detail, the actuator 18 is coupled to the upper plate assembly 14 and moves the upper plate assembly 14 relative to the lower plate assembly 16, the lower plate assembly 16 remaining stationary. In particular, the actuator 18 moves the upper plate assembly 14 through planes parallel with the lower plate assembly 16. Movement of the upper plate assembly 14 away from the lower plate assembly 16 collects sample fluid in a syringe-like drawing manner through a plurality of pipettes in parallel (i.e., simultaneously) as described below. Movement of the upper plate assembly 14 closer to the lower plate assembly discharges collected sample fluid as heretofore unachieved by the prior art and mentioned above.

In the preferred embodiment, the actuator 18 is a pneumatic cylinder which operates along the longitudinal axis of the main shaft area 12 as follows. A user actuates a valve release 20 to open a 3-way valve 22 which in turn allows air to flow into one side of the pneumatic cylinder 18. In turn, a piston 21 in the cylinder is placed under pressure of the air and moves actuator shaft 23 in one direction along the longitudinal axis of the main shaft area 12. The piston 21 moves actuator shaft 23 a certain distance then abruptly stops. To move the actuator 18 in the reverse direction, a spring mechanism is employed. A spring 25 is coupled to piston 21 and lies circumferentially about actuator shaft 23. During the above described movement of actuator shaft 23, piston 21 compresses spring 25. Upon release of the valve release 20, the spring 25 decompresses such that piston 21 and actuator shaft 23 move in the reverse direction.

In moving upward in FIG. 1a, the pneumatic cylinder 18 stops at the repositionable stop 24. The repositionable stop is formed of a fine pitch screw 26 which has markings 28 along its shaft. The user tightens or loosens the screw 26 until a desired marking 28 on the screw shaft is shown. The markings 28 provide an indication of the amount of sample liquid which will be drawn by the actuator 18 stopping at that position of stop 24. Preferably, the markings 28 provide 5 ml increments between a total range of about 20 ml to about 50 ml (for example) to be obtained. In addition, the top or handle portion 30 of the screw 26 provides pointers 31 for indicating fractions of a turn (i.e., less than a full revolution) of the screw 26. Thus, the handle pointers 31 in combination with the screw shaft markings 28 provide an indication to the user of the amount of sample fluid which will be obtained upon the actuator 18 operating to the position set by the repositionable stop 24.

Preferably within the main shaft area 12, the piston 21 comprises aluminum and the actuator shaft 23 comprises stainless steel. The fine pitch screw 26 is stainless steel or of similar material. Other materials are acceptable.

Proceeding with FIG. 1a, the upper plate assembly 14 is coupled to actuator 18 for movement thereby. More accurately, actuator 18 is coupled to upper plate assembly 14 to move the upper plate assembly 14 (i) along a vertical path parallel with the longitudinal axis of main shaft 12 and (ii) from one plane perpendicular to the longitudinal axis to another parallel plane through a series of parallel planes, all the while maintaining the upper plate assembly 14 in-plane (i.e., not tilted across the parallel planes). Upper plate assembly 14 is formed of rod plate 32 having an upper surface 34 and a lower surface 36. Upper surface 34 faces actuator 18 and is coupled to actuator 18 with L-shaped brackets 38. L-shaped brackets 38 are screwed secure to upper surface 34 of plate 32 and collectively provide a seating area in which the foot or distal end of actuator shaft 23 sits by a lateral sliding or snapping-into-position motion. Hence, L-shaped brackets 38 provide removable attachment of plate 32 to actuator 18. The lower surface 36 of plate 32 holds a plurality of metal rods 40 in a desired arrangement/ array for example, in an 8×12 array as discussed above. Rods 40 are about 1.25 inches (31 mm) long and about 0.05 inches in diameter, for example.

Lower plate assembly 16 lies in a plane spaced apart from and parallel with that of upper plate assembly 14. Lower plate assembly 16 is formed of a plate 46 holding a plurality of tubes 42 in a pattern or array matching that of the metal rods 40 of the upper plate assembly 14. Tubes 42 have an inner diameter about in the order of 1000th of an inch (e.g., 0.002 inch) greater than rods 40 outer diameter and a length about matching that of the rods 40. This tight tolerance is sufficient to form a seal with the fluid. The proximal ends of tubes 42 open facing the distal ends of rods 40, each tube 42 facing a respective rod 40 for receiving the same. The proximal ends of tubes 42 are held in holes machined in plate 46. The plate holes have chamfered edges which lie flush with the upper surface 44 of plate 46. The chamfers allow gravity to funnel any extra sample fluid on each of the metal rods 40 after its withdrawal back up through the respective tube 42 toward the proximal end of respective tube 42. Tubes 42 extend through the thickness of plate 46 and have a distal end through which desired samples are obtained as discussed below.

In a preferred embodiment, metal rods 40 and tubes 42 are stainless steel. Plates 32 and 46 are polycarbonate or similar material. In addition rods 40, tubes 42, rod plate 32 and tube plate 46 are of materials that withstand autoclaving in temperatures above about 250° F. (121° C.).

Further, coupled near each corner of tube plate 46 in lower plate assembly 16 is a respective alignment pin 52. Alignment pins 52 provide alignment of tubes 42 with respective metal rods 40 over a subject tray. This is accomplished as follows. A plate holder 50 has a recessed area or seat 54 dimensioned for holding a standard laboratory plate or test tray 58. Different plate holders are used for holding different sized laboratory plates/test trays 58. Plate holder 50 has matching holes 56 in each corner of the holder for receiving distal ends of alignment pins 52. Holes 56 are positioned such that positioning of alignment pins 52 therein aligns the test plate 58 held in plate holder 50 under rod 40-tube 42 pairs. In particular, the wells or predefined work areas of lab plate 58 holding desired sample fluid are aligned so that one such well is under and faces a rod 40-tube 42 pair for each rod 40-tube 42 pair of the upper and lower plate assemblies 14, 16.

Accordingly, each metal rod is aligned with its corresponding tube 42 so that upon operation of the actuator 18, the upper plate assembly 14 simultaneously moves the metal rods 40 along parallel longitudinal axes within tubes 42 for drawing sample fluid from a source lab plate 58, up through tubes 42, to collect desired samples. The same amount of sample fluid is collected in each tube 42 as defined by stop 24 previously set by the user as described above. To subsequently transfer the collected samples, the pipetter system 10 is raised such that alignment pins 52 are released from plate holder 50 and the source plate 58 is exchanged for a target plate 60, i.e., such that the target plate 60 is seated in plate holder 50. Then the pipetter system 10 is lowered so that alignment pins 52 are reseated in respective holes 56 of plate holder 50, and the rod 40-tube 42 pairs are then aligned over the wells of target plate 60 for receiving the collected samples (one well per rod 40-tube 42 pair). The actuator 18 is operated such that the upper plate assembly 14 simultaneously lowers the metal rods 40 into respective tubes 42 to deliver the collected sample liquid into the wells of target tray 60.

In particular, actuator 18 is operated such that metal rods 40 move the collected samples at a sufficiently high velocity, and the metal rods 40 decelerate such that metal rods 40 abruptly stop at the distal end of tubes 42. Such velocity of the sample and abrupt stopping of the metal rods 40 forcing the samples through tubes 42 creates a clean break of the sample from the tip of tubes 42 such that the samples are accurately and in parallel dispensed into respective wells of the target plate 60. Such action by the metal rods 40 within tubes 42 is made possible by the lack of an air gap between the collected samples and the distal ends of metal rods 40. That is, the distal ends of the metal rods 40 are in direct physical contact with the respective collected samples.

In a preferred embodiment, the velocity at which the metal rods 40 move the collected sample is at about 8 to 10 inches per second or greater. The metal rods 40 decelerate over a few 1000th of an inch so that the preferred deceleration is on the order of about 50,000 inches/second$^2$. In addition, the mechanical vibration from such deceleration assists in the samples cleanly breaking free through the distal ends of the tubes 42 into the respective wells of target plate 60.

As an option to the present invention, a working block 48 may be used for elevating a subject test tray 58 in the recessed area 54 of plate holder 50. Working block 48 has dimensions slightly smaller than that of the recessed area 54 of plate holder 50 and is positioned in seat 54 before a subject test plate 58 is placed therein. In turn, the subject test plate 58 is placed on the upper surface of working block 48 positioned in recess 54 of plate holder 50. As a result, the wells of test plate 58 are not only aligned one-to-one with rod 40/tube 42 pairs but are also held closer to the distal ends of tubes 42. This assists in the distal ends of rods 40 making direct contact with sample fluid collected from the wells of test tray 58. Other means for elevating the test plate in the recess 54 of plate holder 50 are suitable.

The upper and lower plate assemblies 14, 16 are designed to be easily replaceable as a unit, thereby allowing the pipetter system 10 to be disassembled for cleaning and allowing several different rod/tube sets (with differing diameters per set) to be used for various volume ranges. Thus, different rod plates 32 and corresponding tube plates 46 can be made and used in a similar manner to that discussed above.

The preferred embodiment for the alignment feature includes four alignment pins 52 attached to the bottom of the tube plate 46 and four corresponding alignment holes in plate holder 50. The alignment pins are interchanged when the tube plate 46/lower plate assembly 16 is interchanged. However, the plate holder 50 may have several sets of alignment holes depending on the type of operation being performed.

For example, one common operation is to withdraw sample fluid from each of the wells of four 96-well plates (source plates) and dispense them into the wells of a single 384-well plate (target plate). The pattern of holes in a conventional 384-well plate is twice the density of holes in the 96-well plate at half the center-to-center distance between the wells. Thus in order to affect the transfer, the plate holder 50 for the 96-well plates have a single set of four alignment holes 56, while the plate holder 50 for the 384-well plate have four sets of four holes. That is, there are four holes 62 a, b, c, d in each corner of the plate holder 50, as illustrated in FIG. 2. One hole 62 of the foursome from each corner correspond to each other, for each of the holes in the foursome. Thus, holes 62a correspond to each other and form one set of alignment holes that receive the alignment pins 52 of lower plate assembly 16. Similarly holes 62b correspond to each other to form a second set of alignment holes, and so forth for holes 62c ad 62d.

For each set of alignment holes 62, when the alignment pins 52 are positioned in a set of alignment holes 62, the pipetter system 10 transfers 96 samples into a corresponding fourth of the 384-well target plate 60. The fourth of the 384-well target plate 60 that corresponds to the set of alignment holes 62a are labeled 64a in FIG. 2. The set of wells 64a include every other well in every other column of wells in target plate 60. The fourth of the target plate 60 that corresponds to the second set of alignment holes 62b include every other well in every odd column of wells in target plate 60. Similarly the fourth of the target plate 60 that corresponds to alignment holes 62c is formed of every odd well in every other column of target plate 60 as illustrated in FIG. 2. Likewise, the fourth of target plate 60 corresponds to the alignment holes 62d is formed of every odd well in every odd column of wells illustrated in target plate 60 in FIG. 2.

An optional tip cleaning system maybe used which will help to avoid cross contamination between different sets of metal rods 40 and corresponding tubes 42. This option uses a wash station with wash fluid in separate wells (one for each metal rod 40). The wash fluid maybe flowing (via pressure) up from the bottom of the well towards the distal ends of metal rods 40. The wash fluid is allowed to overflow over the wells into a drain area which will not allow the wash fluid to come into contact with the fluid in other wells (until it to is in the drain area). Cleaning is affected by lowering the distal ends of metal rods 40 into the wash wells and operating the actuator 18 several times so that metal rods 40 are raised and lowered through corresponding tubes 42 several times.

Housing 70 envelopes/covers the main shaft area 12, upper plate assembly 14 and lower plate assembly 16. In addition, the portion of housing 70 that covers main shaft area 12 provides a handle for ease of use. That is the handle is dimensioned (about 10–12 inches around and about 4 or 5 inches long, for example) so that the pipetter system 10 is easy to grip and hold during hand held use.

In addition, a bracket assembly 68 is coupled to the lower portion of housing 70. Bracket assembly 68 provides a seat area for holding the edges of plate 46 of the lower plate assembly 16. That is, the edges of tube plate 46 are laterally slid into the seat area of bracket assembly 68 such that the lower plate assembly 16 is removably secured to housing 70. In the preferred embodiment, the same lateral sliding motion for coupling tube plate 46 to bracket assembly 68 engages the foot of the actuator 18 into the L-shaped brackets 38 of the upper plate assembly 32, described above. To that end, with the upper plate assembly 14 and lower plate assembly 16 held as a unit, one lateral sliding motion removably couples the upper plate assembly 14 to the actuator 18 and the lower plate assembly 16 to housing 70.

Further, housing 70 comprises plastic to maintain the pipetter system's light weight. This is consistent with the materials of each major piece of the pipetter system 10 as described above which in the preferred embodiment are chosen for minimizing overall weight of the system. The easy to handle design and relative light total weight provide a hand held pipetter system 10.

Figure 1B:
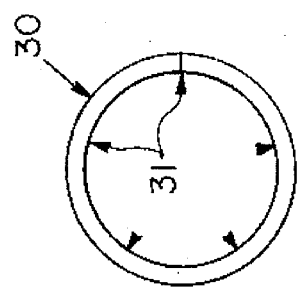
Figure 3:
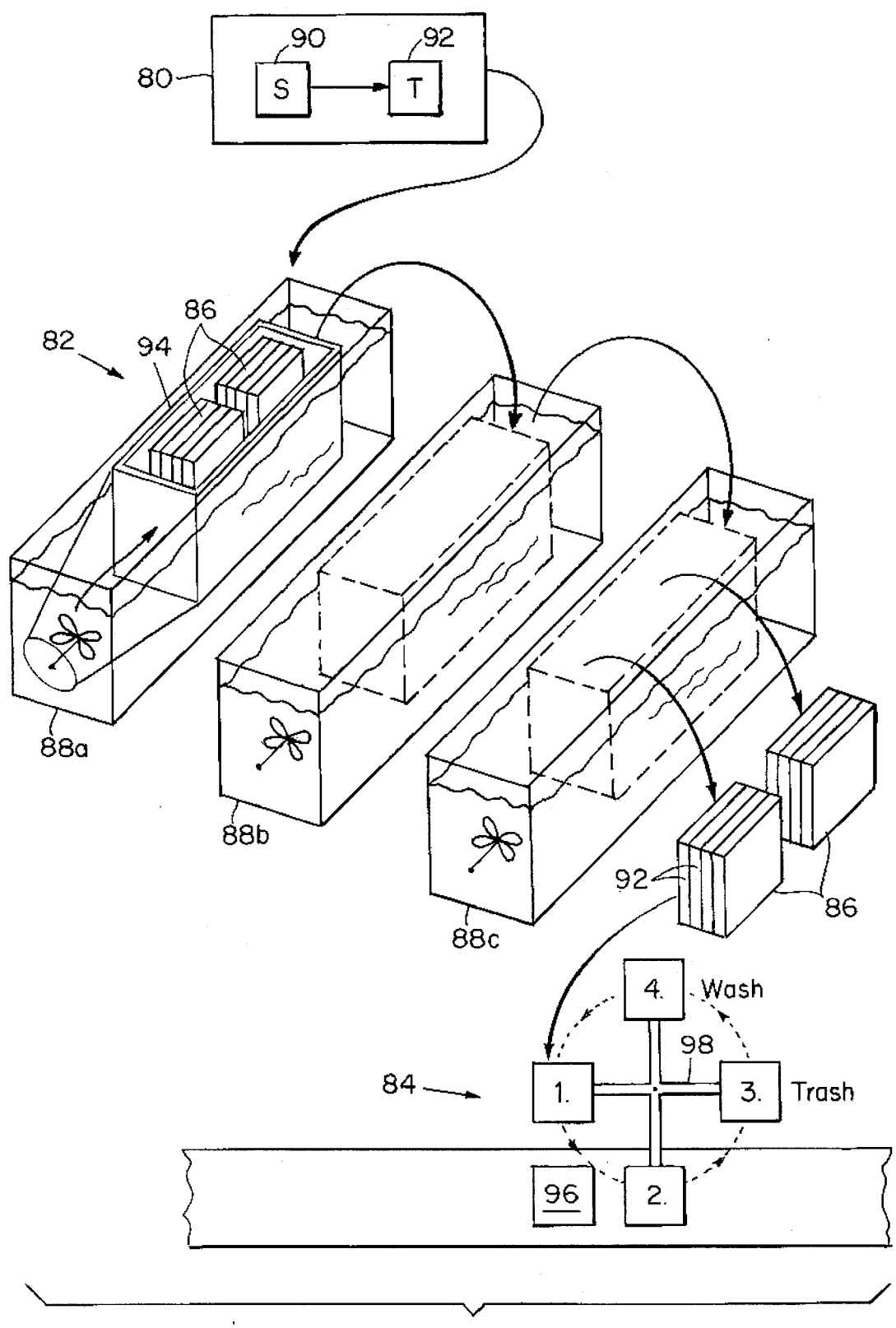
FIG. 3 is a schematic diagram of a lab system employing an embodiment of the present invention.

It is understood that the pipetter system may be used in other systems or machines instead of in a hand held manner by a human user. For example, as illustrated in FIG. 3, a pipetter system of the present invention can be employed in a mechanized system for processing biological samples. By way over overview, the mechanized system employs three work areas. A first work area 80 assembles laboratory plates with desired samples and heat seals the plates. In particular, a pipetter system of the present invention as illustrated in FIGS. 1a–1b is employed to collect the samples from a source plate 90 and dispense the samples to a target plate 92.

The second work area 82 provides washing and heating of the collected samples. In particular, two racks 86 of 48 (for example) prepared target plates 92 are processed through a trio temperature cycle. In the preferred embodiment, three different water baths 88 *a, b, c* are utilized, each bath providing heating of the target plates 92 at a different temperature. A set or racks 86 of target plates 92 is positioned in a working bin 94 over each of the baths 88 one bath at a time. While positioned over a bath 88, a propeller pumps water up through a duct to the bin 94. The water runs through the bin 94, across the target plates 92 to the ends of the bin and back into the bath 88. The flow of water provides uniform heating of the target plates 92.

After processing through the temperature cycle, the target plates 92 are processed in a third work area 84. The third work area involves transferring the samples (i.e., target plates 92) from the racks 86 used in the second work area 82, stacking sample plates 92 onto a membrane plate 96, poking holes in the sample plate 92, and sucking the sample to the membrane plate 96.

To accomplish the foregoing, a carousal type conveyer is employed. At the first position of the carousal 98, the sample is layered on top of a filter or membrane 96. At the second position of the carousal 98, a bed of nails or pins is held and is used to press through the sample plate 92 to the membrane 96. At the same time, a vacuum is drawn through the filter 96 to suck the collected sample fluid from the sample plate 92 onto the membrane 96. At the third position of the carousal 98, the sample plate 92 is disposed of. And at the fourth position of the carousal 98, the nails/pins are washed.

Other uses for the invention pipetter system are open, the foregoing uses being for purposes of illustration and not limitation.

Equivalents

While the invention has been particularly shown and described with reference to a preferred embodiment thereof, it will be understood by those skilled in the art that various changes in form and details may be made therein without departing from the spirit and scope of the invention as defined by the appended claims.

For example, although the embodiment described in FIGS. 1a–1b employs a pneumatic cylinder for dispensing samples and a spring mechanism for collecting samples, it is understood that manual, hydraulic or motorized versions for operating either or both directions of movement of the actuator 18 and hence movement of upper plate assembly 14 with respect to lower plate assembly 16 are within the purview of one skilled in the art. Likewise pneumatic operation of the actuator 18 in both directions or spring/mechanical operation of actuator 18 in both directions is within the purview of those skilled in the art.

We claim:

1. A pipetter system for pipetting in parallel through a plurality of pipettes comprising:

an actuator for operation along a longitudinal axis;

an upper plate assembly holding a plurality of rods, the upper plate assembly coupled to the actuator for movement by the actuator through a series of planes that are perpendicular to the longitudinal axis, such that the upper plate assembly lies in a plane perpendicular to the longitudinal axis, each rod having a working end spaced from and facing away from the upper plate assembly; and a lower plate assembly (i) lying in a plane spaced apart from and parallel to the plane of the upper plate assembly, and (ii) holding a plurality of tubes for receiving the rods, working end first, of the upper plate assembly, there being a different rod for each tube and each rod being axially aligned with its respective tube, each tube having a proximal end through which the respective rod is received and a distal end opposite the proximal end, upon the actuator moving the upper plate assembly with respect to the lower plate assembly the rods simultaneously traverse the length of the respective tubes, the rods traversing the length of the respective tubes from the distal ends to the proximal ends of the tubes collecting sample fluid in each tube, and the rods traversing the length of the respective tubes from the proximal end to the distal end dispensing collected sample fluid, the working end of each rod being in direct contact with the collected sample fluid of the respective tube, wherein the actuator moves the upper plate assembly in a manner such that when the rods traverse the length of the respective tubes from the proximal ends to the distal ends of the tubes sufficient velocity is imparted to the collected sample fluid to enable collected sample fluid to cleanly exit the distal ends of the tubes and wherein the actuator abruptly stops movement of the upper plate assembly such that the rods are abruptly stopped at the distal ends of the respective tubes and the collected sample fluid under inertia exits the respective tubes and wherein each rod has an outer diameter on the order of 1000th of an inch smaller than the inner diameter of the respective tube such that when the rods traverse the length of the respective tubes, each rod has a sufficiently small gap between the rod along its length and inner walls of the respective tube that, with the fluid, forms a seal and maintains the working end of the rod in contact with the sample fluid, enabling each tube to be free of mechanical seals.

2. A pipetter system as claimed in claim 1 wherein for each tube, the lower plate assembly has a chamfered opening for holding the tube such that sample fluid is funneled into the proximal end of the tube.

3. A pipetter system as claimed in claim 1 wherein the actuator is of pneumatic, manual or motorized operation.

4. A pipetter system as claimed in claim 1 further comprising:

a spring mechanism for enabling the actuator to move the upper plate assembly such that the rods traverse the length of the respective tubes from the distal ends to the proximal ends of the tubes for collecting sample fluid in each tube; and an adjustable stop positioned adjacent the actuator for stopping upward movement of the upper plate assembly and hence stopping movement of the rods along the length of the respective tubes from the distal ends to the proximal ends of the respective tubes, such that a certain amount of sample fluid is collected in each tube, the position of the stop (i) determining amount of sample fluid able to be collected in each tube and (ii) being predetermined by a user such that a desired amount of sample fluid is collected in each tube.

5. A pipetter system as claimed in claim 4 wherein the adjustable stop includes a screw formed of a shaft and a head, the screw shaft having markings for indicating certain increments of sample fluid which will be collected when the screw is turned to that marking, and the screw head providing indications of fractions of the shaft increments such that position of the screw provides an indication of the amount of sample fluid to be obtained with the screw at that position.

6. A pipetter system as claimed in claim 1 wherein the lower plate assembly further includes alignment pins extending therefrom, and the pipetter system further comprises a holder having (i) a vertical recessed area for holding a subject tray, the tray having a plurality of predefined work areas, and (ii) a plurality of holes outside the vertical recessed area for receiving the alignment pins of the lower plate assembly to align the distal ends of the tubes and respective rods with the work areas of the subject tray.

7. A pipetter system as claimed in claim 6 wherein a subset of the holes of the holder receive the alignment pins of the lower plate assembly for aligning the distal ends of the tubes and respective rods with a subset of the work areas of the subject tray, and a different subset of the holes of the holder receive the alignment pins of the lower plate assembly for aligning the distal ends of the tubes and respective rods with a different subset of the work areas of the subject tray.

8. A pipetter system has claimed in claim 6 further comprising vertical elevation means in the vertical recessed area of the holder, the elevation means for positioning the working areas of the subject tray closer to the distal ends of the tubes and respective rods.

9. A pipetter system as claimed in claim 1 wherein the upper plate assembly further includes brackets for removably coupling the upper plate assembly to the actuator.

10. A pipetter system as claimed in claim 1 further comprising a housing for enclosing the actuator, upper plate assembly and lower plate assembly, the housing providing a handle for hand held use of the pipetter system.

* * * * *